United States Patent
Ji

(10) Patent No.: US 8,309,617 B2
(45) Date of Patent: Nov. 13, 2012

(54) RECYCLING METHANE-RICH PURGE GAS TO GASIFIER

(75) Inventor: Shuncheng Ji, Katy, TX (US)

(73) Assignee: Phillips 66 Company, Houston, TX (US)

( * ) Notice: Subject to any disclaimer, the term of this patent is extended or adjusted under 35 U.S.C. 154(b) by 293 days.

(21) Appl. No.: 12/784,642

(22) Filed: May 21, 2010

(65) Prior Publication Data

US 2011/0160313 A1 Jun. 30, 2011

Related U.S. Application Data

(60) Provisional application No. 61/291,677, filed on Dec. 31, 2009.

(51) Int. Cl.
*C07C 27/00* (2006.01)
*C07C 1/02* (2006.01)
*C01B 3/24* (2006.01)

(52) U.S. Cl. ........ 518/702; 518/700; 518/703; 518/704; 518/705; 423/650

(58) Field of Classification Search .................... 518/702
See application file for complete search history.

(56) References Cited

U.S. PATENT DOCUMENTS

2009/0324462 A1 * 12/2009 Robinson et al. ............. 422/187

* cited by examiner

*Primary Examiner* — Shawquia Young
(74) *Attorney, Agent, or Firm* — Phillips 66 Company

(57) ABSTRACT

A process for improving the overall carbon conversion efficiency of a gasification process, as well as improving the suitability of a syngas containing 0.5-10% methane for use as a feedstock for chemical production. A gasification reactor converts carbonaceous feedstock to syngas that is, in turn, utilized for a chemical production process in a chemical production reactor. An off-gas from this chemical production reactor is directed to a selective membrane that separates the off-gas into methane-rich and hydrogen-rich fractions. The hydrogen-rich fraction, is re-utilized as feedstock for the chemical production process, while the methane-enriched fraction is returned to the gasification reactor to form additional syngas.

16 Claims, 2 Drawing Sheets

RECYCLING METHANE-RICH PURGE GAS TO GASIFIER

FIELD OF THE DISCLOSURE

The present invention relates to an improved gasification system and process that converts carbonaceous feedstock into desirable gaseous products such as synthesis gas. More specifically, the present disclosure relates to improvements in the efficiency of the gasification process, while simultaneously improving the suitability of the synthesis gas thereby produced for utilization in certain downstream chemical applications.

BACKGROUND

Gasification processes are widely used to convert solid or liquid feedstocks such as coal, petroleum coke and petroleum residue into synthesis gas. Synthesis gas is predominantly composed of hydrogen gas ($H_2$) and carbon monoxide (CO), and is utilized both as fuel for the production of electricity, as well as a feedstock for producing chemicals such as hydrogen, methanol, ammonia, synthetic natural gas or synthetic transportation oil.

Synthesis gas produced via the gasification of carbonaceous material commonly contains some methane. The relative quantity of methane in the synthesis gas varies with the type of gasification system utilized, but is often observed to be higher in two-stage gasification systems. For example, the synthesis gas produced in ConocoPhillips E-Gas™ two-stage gasifier usually contains between 1.5-4% methane (dry vol.) This quantity of methane produced is not of significant concern when the synthesis gas is utilized as fuel for gas combustion turbines that produce electricity. However, the presence of methane is not desirable when the synthesis gas is to be utilized as a feedstock for the production of value-added petrochemicals.

Known chemical production methods utilizing synthesis gas commonly involve converting $H_2$ and CO from the raw synthesis gas into liquid products. Methane is often an inert gas for these syngas conversion processes. Thus, the purge gas leaving the chemical conversion reactor is often rich in methane. This purge gas is commonly combusted as a fuel gas, resulting in a reduction of the overall carbon conversion efficiency. Accordingly, there exists a need for improved processes and systems that can increase the overall carbon conversion efficiency of the gasification process, thereby maximizing the production of hydrogen and CO for a given quantity of feedstock. The invention described herein provides a unique process for improving the overall carbon conversion efficiency of the gasification process by recycling the methane-rich purge gas back to the gasification reactor where the methane-rich gas is converted to syngas via the steam-methane reforming reaction.

BRIEF DESCRIPTION

The present invention, provides a method for gasifying a carbonaceous feedstock. The method generally comprises partially oxidizing the feedstock in a gasification reactor to thereby produce a product gas comprising $H_2$, CO, and methane. In certain embodiments, the methane content of the product gas is generally between about 0.5% and 10% by volume. This methane is separated from the product gas, and conveyed back to the gasification reactor, thereby increasing overall process efficiency. Certain embodiments of the invention comprise a process that includes the following steps: a) providing a gasification reactor; b) partially oxidizing a carbonaceous feedstock in said reactor to produce a product gas comprising $H_2$, CO, and methane; c) separating the product gas into a hydrogen-rich gas stream, and a methane-rich purge gas stream; and d) routing the methane-rich purge gas stream to a compressor, and then back to the gasification reactor, wherein the methane-rich purge gas stream serves as carbonaceous feedstock for the production of said product gas of part b). The molar fraction of methane in the methane-rich purge gas may be between about 10% and about 75%, but preferably it is between about 25% and about 65%.

In certain embodiments, the separation of product gas into a hydrogen-rich gas stream and a methane-rich purge gas stream is performed by a selectively-permeable membrane. In certain embodiments, the gasification reactor comprises a first reaction zone and a second reaction zone, wherein a partial oxidation of the feedstock is the predominant reaction occurring within the first reaction zone, while pyrolysis of the feedstock is the predominant reaction occurring within the second reaction zone. In certain embodiments, the methane-rich purge gas stream of step c) is routed to a compressor, then to the first reaction zone of the gasification reactor. In the gasification reactor, the methane-rich purge gas stream is converted to carbon monoxide and hydrogen gas primarily via the methane-steam reforming reaction: $CH_4 + H_2O \rightarrow CO + 3H_2$. This maximizes the production of hydrogen and carbon monoxide from the carbonaceous feedstock, thereby increasing process efficiency. Indeed, certain embodiments of the current invention decrease the overall rate of carbonaceous feedstock consumption by said gasification reactor by at least 2% per hour (by weight). Other embodiments decrease carbonaceous feedstock consumption by at least 5% per hour, while also reducing oxygen consumption.

In certain embodiments, the hydrogen-enriched (and methane-depleted) gas stream created by the selectively-permeable membrane-based separation is utilized as a feedstock for a chemical production process that may comprise a Fischer-Tropsch process, or a process for the production of methanol, ammonia, methyl acetate, urea, urea ammonium nitrate, or hydrogen, etc.

BRIEF DESCRIPTION OF THE DRAWINGS

Advantages of the present invention will become apparent to those skilled in the art with the benefit of the following description and upon reference to the accompanying drawings.

Figure 1:
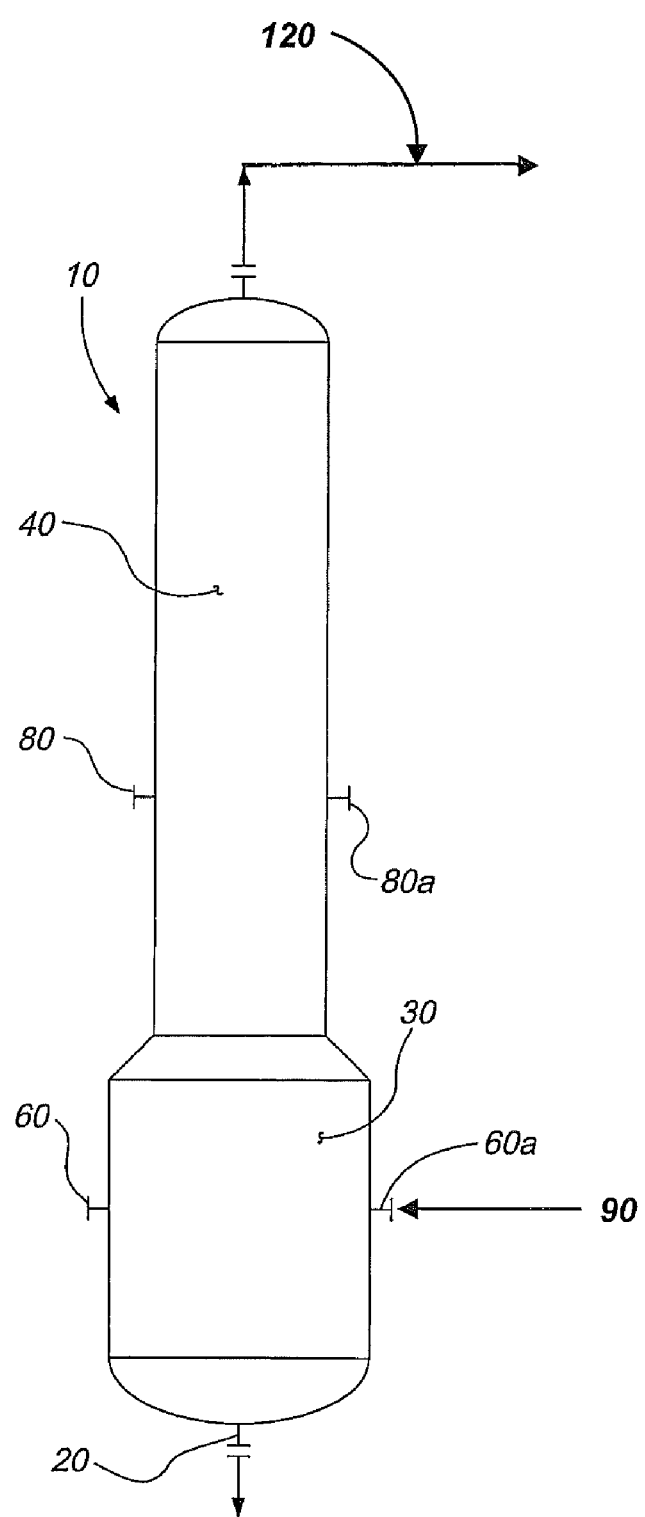
FIG. 1 is a schematic illustration in accordance with one embodiment of the current invention that depicts a two-stage gasification reactor, showing the relative positioning of the stages, as well as inlets for carbonaceous feed stock and methane-rich purge gas.

The invention is susceptible to various modifications and alternative forms, specific embodiments thereof are shown by way of example in the drawings. The drawings may not be to scale. It should be understood that the drawings and their accompanying detailed descriptions are not intended to limit the scope of the invention to the particular forms disclosed, but rather, the intention is to cover all modifications, equivalents and alternatives falling within the spirit and scope of the present invention as defined by the appended claims.

DETAILED DESCRIPTION

The present invention is applicable to any gasification system wherein the overall efficiency of the process can be improved by separating hydrogen from an off-gas stream produced as a by-product of downstream chemical processes that utilize synthesis gas as a feedstock, thereby producing a methane-rich purge gas. Such downstream processes may include, but are not limited to, a coal-to-liquids plant (CTL), or the production of hydrogen, ammonia, urea, hydrogen or methanol. Processes for the gasification of carbonaceous materials are well-known in the art, and will be described herein only in the detail required to fully disclose the present invention. In certain embodiments, the present invention builds upon the disclosures of U.S. Provisional Patent Applications 61/165,784, 61/138,312, 61/165,784, and 61/146, 189, as well as U.S. patent application Ser. Nos. 12/192,471 and 11/834,751, which are all hereby incorporated by reference in their entirety.

In certain embodiments of the current invention, gasification is accomplished by partial combustion of a carbonaceous feedstock with a small quantity of air or high purity oxygen in a gasification reactor, creating hot synthesis gas predominantly comprising hydrogen, carbon monoxide and methane. The residual mineral content of the carbonaceous feedstock forms a molten slag that is continuously removed from the gasifier. The hot synthesis gas created in a first reaction zone flows into a second reaction zone where it provides the heat required for the gasification of additional carbonaceous feedstock introduced into the second reaction zone. The synthesis gas exiting the gasification reactor is cooled and cleaned of particulates and chemical contaminants, and is then conditioned further prior to use as a feedstock for a process for the production of chemicals such as hydrogen, methyl acetate, methanol, urea, urea ammonium nitrate, ammonia, Fischer-Tropsch liquids, etc.

Referring to FIG. 1, certain embodiments of the present invention provide a two-stage gasification reactor 10, that comprises first and second reaction zones. The first reaction zone comprises a reactor lower-section 30, while the second reaction zone comprises a reactor upper-section 40. In FIG. 1, the unfired reactor upper-section 40 of the reactor 10 is directly attached to the top of the fired reactor lower-section 30 of the reactor 10 so that the hot reaction products of the first reaction zone are conveyed directly from the reactor lower-section 30 to the second reaction zone of the reactor upper-section 40, thereby minimizing heat loss.

Further referring to FIG. 1, the gasification process begins within the first reaction zone (or reactor lower-section 30), when a carbonaceous feedstock is mixed with a gas stream comprising an oxygen-containing gas and/or steam and a rapid exothermic reaction takes place in which the carbonaceous feedstock is converted into a first mixture product comprising steam, synthesis gas, intermediate gases, and entrained by-products such as ash. Ash is comprised of the non-combustible mineral content of the carbonaceous feedstock. The temperature of the first reaction zone is maintained higher than the ash melting point, which allows the ash that is formed to melt and agglomerate to form a viscous liquid known as slag. The slag falls to the bottom of the reactor lower-section 30 and flows through a taphole 20, whereupon it is water-quenched and directed to a slag processing system (not shown) for final disposal.

The primary combustion reactions occurring in the first reaction zone are $C+O_2 \rightarrow CO_2$ and $$C + \frac{1}{2}O_2 \rightarrow CO,$$

which are highly exothermic. The exothermic reactions raise the temperature in the first reaction zone to between 2000° F. and 3500° F. The heat produced in the first reaction zone is carried upward with the gas stream, thereby providing heat for pyrolysis reactions that occur in the unfired second reaction zone, including vaporization of water injected into the second reaction zone as part of a feedstock slurry (for those embodiments that utilize a slurrified feedstock), the carbon-steam reaction ($C+H_2O \rightarrow CO+H_2$) and the water-gas shift reaction ($CO+H_2O \rightarrow CO_2+H_2$). The carbon-steam reaction forms CO and $H_2$, thereby increasing the yield of these usable gases. The steam utilized during the gasification process may be generated from the heat recovery unit (not shown), which in turn, derives its heat from the hot synthesis gas exiting the upper section 40 of the gasification reactor 10 shown in FIG. 1.

In the embodiment shown in FIG. 1, a pulverized solid stream of carbonaceous feedstock is injected into the second reaction zone (or upper-section 40) through feeding device 80 and/or 80a. In certain alternative embodiments (not depicted) alternative feeding devices, such as, but not limited to, slurry feeding systems or dry feeding systems, can be utilized to add feedstock to the gasification reactor.

The reaction conditions in the second reaction zone (or reactor upper-section 40) are controlled to assure rapid gasification and heating of the feedstock above its range of plasticity. Once dispersed into the reactor upper-section, the feedstock comes into contact with the hot first mixture product rising from the first reaction zone (or reactor lower-section 30). The carbonaceous feedstock is dried as the water in the slurry turns to steam, and a portion of the feedstock is gasified via pyrolysis reactions such as the carbon steam reaction to produce hydrogen and carbon monoxide.

Further referring to FIG. 1, the raw gas stream 120 exiting the second reaction zone (or reactor upper-section 40) of the gasification reactor 10 may comprise one or more of the following: carbon monoxide (CO), carbon dioxide ($CO_2$), hydrogen ($H_2$), water ($H_2O$), methane ($CH_4$) and other light hydrocarbons, and nitrogen ($N_2$). Additionally, the raw gas stream can comprise one or more undesirable components (i.e., contaminants) that should be removed prior to utilizing the raw gas stream for the production of chemicals. Sulfur compounds, such as, for example, hydrogen sulfide ($H_2S$), carbonyl sulfide (COS), carbon disulfide ($CS_2$), and even organosulfur compounds such as mercaptans and various thiophenic compounds are a few examples of common contaminants found in the raw gas stream. Other examples of contaminants typically present in the raw gas stream can include, but are not limited to, ammonia ($NH_3$), hydrochloric acid (HCl) and hydrogen cyanide (HCN).

Table 1, below, summarizes the composition of the raw synthesis gas stream according to one embodiment of the present invention.

TABLE 1

| | Components in Raw Gas Stream (based on total stream volume) | | |
|---|---|---|---|
| Component | Broad Range | Intermediate Range | Narrow Range |
| $H_2$ | 8-50 vol % | 10-40 vol % | 15-35 vol % |
| CO | 10-75 vol % | 15-60 vol % | 25-50 vol % |
| $CO_2$ | 1-40 vol % | 5-30 vol % | 7-20 vol % |
| $H_2O$ | 4-40 vol % | 8-30 vol % | 10-25 vol % |
| $H_2S$ | 0.001-5 vol % | 0.1-2.5 vol % | 0.5-2 vol % |
| $CH_4$ | 0.05-10 vol % | 0.1 to 7.5 vol % | 0.5 to 5.0 vol % |

TABLE 1-continued

Components in Raw Gas Stream
(based on total stream volume)

| Component | Broad Range | Intermediate Range | Narrow Range |
|---|---|---|---|
| COS | 100-5,000 ppmv | 200-2,500 ppmv | 350-1,500 ppmv |
| HCl | 50-2,000 ppmv | 100-1,500 ppmv | 250-1,000 ppmv |
| $NH_3$ | 50-2,000 ppmv | 100-1,500 ppmv | 250-1,000 ppmv |
| Other (total) | <2.5 vol % | <2.0 vol % | <1 vol % |

It can be seen from Table 1 that the raw syngas stream may contain a significant amount of methane (up to 10% by volume). Methane is not a useful feedstock component for many chemical processes that utilize the $H_2$ and CO components of synthesis gas as a starting material. Thus, in these processes, the overall efficiency of carbon utilization is decreased relative to gasification processes that produce less methane. The embodiments disclosed herein provide a mechanism for increasing the efficiency of carbon utilization by recovering methane from the downstream off-gas and converting it to carbon monoxide and hydrogen in the first reaction zone of the gasification reactor.

Figure 2:
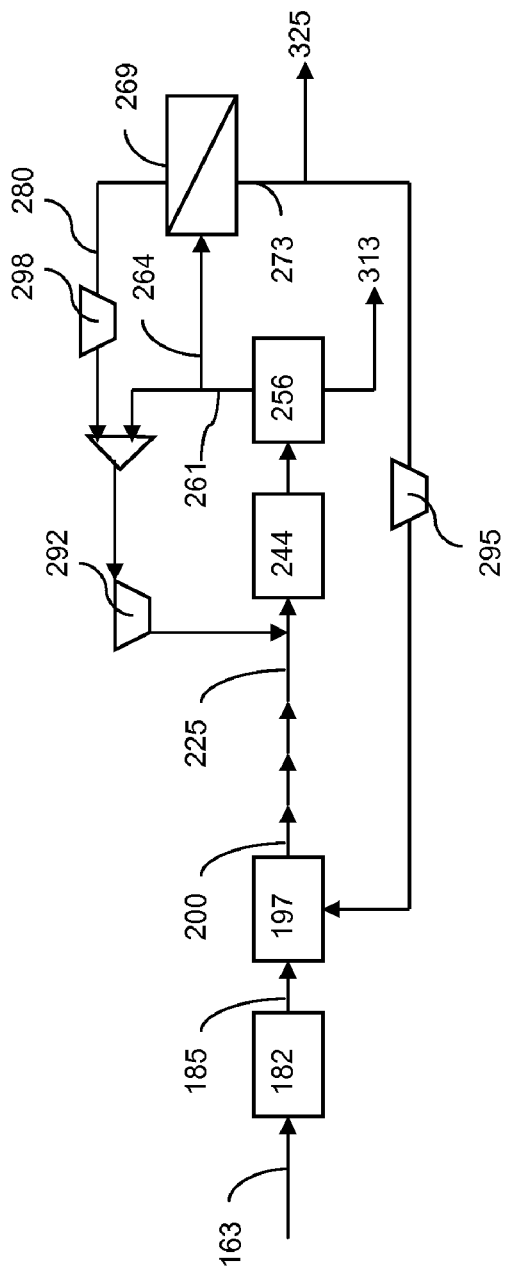
FIG. 2 is a flow diagram of a gasification system utilized for the production of methanol, which is in accordance with an embodiment of the current invention.

FIG. 2 is a schematic flowchart representing one embodiment of the current invention. However, the process of the current invention is applicable to a variety of different chemical production processes (as described) that utilize the components of synthesis gas as a feedstock. The embodiment depicted in FIG. 2 begins with a carbonaceous feedstock 163 being pulverized in a mill 182 and combined with water to form a slurry 185. The slurry is then fed to a gasification reactor 197 to produce a product gas, or raw synthesis gas 200. The high-temperature raw synthesis gas is then cooled, and both particulates and acid gases are removed via methods that are commonly known to those skilled in the art and that are outside the scope of this document (not depicted). These methods provide a cleaned and cooled synthesis gas that is suitable for use as a feedstock for a variety of chemical production processes.

Further referring to FIG. 2, the cleaned and cooled synthesis gas 225 is fed to a methanol reactor 244 containing a methanol conversion catalyst (not depicted), wherein the catalyst converts the $H_2$ and CO present in the synthesis gas to methanol. Methods for producing methanol are well known in the art, and outside the scope of this disclosure. The gas mixture exiting the methanol reactor 244 is cooled and the resultant vapor-liquid mixture flows to a catch pot 256, wherein liquid methanol is drained from the bottom of the catch pot as a crude methanol product 313, while un-reacted off-gas 261 is split into two streams. One stream is recycled back to the methanol reactor, while the other stream 264 flows to a membrane separation unit 269 that contains a selectively-permeable membrane. In the embodiment depicted in FIG. 2, this membrane is selectively permeable to hydrogen, but relatively impermeable to methane and carbon monoxide. The membrane separation unit separates the gas into methane-rich purge gas 273 and hydrogen-rich gas 280 components. The hydrogen-rich gas 280 flows to a compressor 298 that compresses the gas and combines it with any un-reacted off-gas 261 that was not routed to the membrane separation unit 269. The combined un-reacted off-gas 261 and hydrogen-rich gas 280 flow to a recycle compressor 292 prior to combining with the raw syngas stream 225 just upstream from the methanol reactor 244. This allows these recycled streams 261 and 280 to again be utilized as feedstock for methanol production. Meanwhile, a portion of the methane-rich purge gas 273 may be routed to flare 325 in order to prevent the accumulation of inert gases such as nitrogen and argon. The portion of the methane-rich purge gas 273 that is not purged is compressed in a compressor 295, and the compressed gas is routed to the gasification reactor 197 to be once again used as feedstock for syngas production. In certain embodiments that utilize a two-stage gasification reactor, the methane-rich purge gas is recycled to the first stage of the reactor 90 (shown in FIG. 1). In certain alternative embodiments (not depicted), the membrane utilized may instead be selectively permeable to methane, and the process of the invention is easily adapted to this change in permeability. Methane can also be separated from the off-gas using other methods such as pressure swing adsorption or lean oil absorption. The use of these methods is common in industrial processes, and easily implemented by those of average skill in the art.

EXAMPLE 1

Process simulations were performed to assess whether recycling a methane-rich purge gas to the first stage of a two-stage, wet slurry-fed gasification reactor would decrease the overall rate of coal feedstock consumption required to produce a given amount of carbon monoxide and hydrogen. The feedstock composition used for these simulations was a bituminous coal with a total moisture of 11.6% (by wt), and elemental analysis (by wt, dry basis) as follows: Carbon: 72.38%, Hydrogen: 4.42%, Nitrogen: 0.78%, Oxygen: 12.43%, Sulfur: 0.79%, and Ash: 9.20%. The heating value was 5957 kcal/kg, and the initial deformation temperature was 1090° C.

The composition of a typical methane-rich purge gas is as shown in Table 2. A typical temperature and pressure of the purge gas is 40° C. and 7.4 MPa.

TABLE 2

Purge Gas Molar Composition

| Compound | Molar Fraction |
|---|---|
| Methane | 0.4537 |
| Carbon Monoxide | 0.2660 |
| Hydrogen | 0.2279 |
| Nitrogen | 0.0381 |
| Carbon Dioxide | 0.0101 |
| Argon | 0.0038 |

The composition of the methane-rich purge gas (detailed above in Table 2) was utilized to calculate the impact of recycling a methane-rich purge gas to the gasification reactor on overall consumption of coal feedstock and oxygen. The results of these calculations are provided below in Table 3. The results demonstrate that returning the methane-rich purge gas to the gasification reactor decreased the rate of coal usage by 9%, and the amount of $O_2$ usage by 2%. This decrease in the consumption of coal and oxygen reflects a significant increase in the overall efficiency of the gasification process.

TABLE 3

| | No Purge Recycle | With Purge Recycle | % Change |
|---|---|---|---|
| Impact of Purge Gas Recycle to Gasification Reactor on Coal and $O_2$ Consumption | | | |
| Coal usage (tons/hr) | 124.9 | 113.2 | −9.0% |
| O2 usage (tons/hr) | 93.0 | 91.1 | −2.0% |

TABLE 3-continued

|  | No Purge Recycle | With Purge Recycle | % Change |
|---|---|---|---|
| $CH_4$ Recycle Ratio | 0 | 0.69 | |
| Impact of Purge Gas Recycle to Gasification Reactor on Scrubbed Syngas Composition | | | |
| $H_2$ (vol %) | 21.4 | 22.4 | 4.7% |
| CO | 30.6 | 29.0 | −5.2% |
| $CH_4$ | 2.5 | 2.5 | |
| $CO_2$ | 12.9 | 12.5 | |
| $N_2$ | 0.2 | 0.4 | |
| $H_2S$ | 0.2 | 0.2 | |
| $NH_3$ | 0.5 | 0.5 | |
| $H_2O$ | 31.6 | 32.5 | |

DEFINITIONS

For the purposes of this disclosure, the term "syngas" is synonymous with synthesis gas or synthetic gas, the term "gas" is synonymous with methane, natural gas, as well as gasoline or any other liquid hydrocarbon fuel.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed and certain features of the invention may be utilized independently, all as would be apparent to one skilled in the art after having the benefit of this description of the invention. Changes may be made in the elements described herein without departing from the spirit and scope of the invention as described in the following claims.

I claim:

1. A process comprising:
   a) providing a gasification reactor;
   b) partially oxidizing a carbonaceous feedstock in said reactor to produce a product gas comprising $H_2$, CO, and methane;
   c) utilizing the product gas as feedstock for a chemical synthesis reactor to thereby produce a reaction product and an off-gas stream;
   d) separating the off-gas stream into a hydrogen-rich gas stream, and a methane-rich purge gas stream;
   e) compressing the methane-rich purge gas stream, then routing said stream back to the gasification reactor, wherein said methane-rich purge gas stream serves as carbonaceous feedstock for additional production of said product gas of part b).

2. The process of claim 1, wherein the separation of part d) is performed by a selective membrane.

3. The process of claim 1, wherein the gasification reactor comprises a first reaction zone and a second reaction zone, and wherein a partial oxidation of the feedstock is the predominant reaction occurring within the first reaction zone, while pyrolysis of the feedstock is the predominant reaction occurring within the second reaction zone.

4. The process of claim 3, wherein the methane-rich purge gas stream is compressed, then routed to the first reaction zone of the gasification reactor.

5. The process of claim 1, wherein the methane-rich purge gas stream of part e) is converted to carbon monoxide and hydrogen gas in the gasification reactor via the steam-methane reforming reaction: $CH_4+H_2O \rightarrow CO+3H_2$.

6. The process of claim 1, wherein said hydrogen-rich gas stream is utilized as a feedstock for a chemical production process that may comprise a Fischer-Tropsch process, or a process for the production of methanol, methyl acetate, urea, urea ammonium nitrate, ammonia or hydrogen.

7. The process of claim 1, wherein the overall rate of carbonaceous feedstock consumption is decreased by about 2% (by weight) or more.

8. The process of claim 1, wherein the amount of oxygen required for partially oxidizing said carbonaceous feedstock is decreased.

9. The process of claim 1, wherein the methane content of the product gas of part a) is between about 0.5% and 10% by weight.

10. The process of claim 1, wherein the molar fraction of methane in the methane-rich purge gas is between about 10% and about 75%.

11. The process of claim 1, wherein the molar fraction of methane in the methane-rich purge gas is between about 25% and about 65%.

12. A process comprising:
   a) providing a gasification reactor;
   b) partially oxidizing a carbonaceous feedstock in said reactor to produce a product gas comprising $H_2$, CO, and methane;
   c) utilizing the product gas as feedstock for a chemical synthesis reactor to thereby produce a reaction product and an off-gas stream;
   d) separating the off-gas stream into a hydrogen-rich gas stream, and a methane-rich purge gas stream,
      wherein said separation is performed by a selective membrane;
   e) compressing the methane-rich purge gas stream, then routing said stream back to the gasification reactor,
      wherein said methane-rich purge gas stream serves as carbonaceous feedstock for additional production of said product gas of part b), and
      wherein the methane-rich purge gas stream is converted to carbon monoxide and hydrogen gas in the gasification reactor via the steam-methane reforming reaction:

$$CH_4+H_2O \rightarrow CO+3H_2.$$

13. A process comprising:
   a) providing a gasification reactor;
      wherein the gasification reactor comprises a first reaction zone and a second reaction zone,
      and wherein a partial oxidation of the feedstock is the predominant reaction occurring within the first reaction zone, while pyrolysis of the feedstock is the predominant reaction occurring within the second reaction zone;
   b) partially oxidizing a carbonaceous feedstock in said reactor to produce a product gas comprising $H_2$, CO, and methane;
   c) utilizing the product gas as feedstock for a chemical synthesis reactor to thereby produce a reaction product and an off-gas stream;
   d) separating the off-gas stream into a hydrogen-rich gas stream, and a methane-rich purge gas stream,
      wherein said separation is performed by a selective membrane;

e) compressing the methane-rich purge gas stream, then routing said stream back to the gasification reactor,
wherein said methane-rich purge gas stream serves as carbonaceous feedstock for additional production of said product gas of part b), and
wherein said methane-rich purge gas stream is routed to the first reaction zone of the gasification reactor, and
wherein the methane-rich purge gas stream is converted to carbon monoxide and hydrogen gas in the gasification reactor via the steam-methane reforming reaction:

$$CH_4 + H_2O \rightarrow CO + 3H_2.$$

14. The process of claim 12 or 13, wherein the overall rate of carbonaceous feedstock consumption by said gasification reactor is decreased by about 2% (by weight) or more.

15. The process of claim 12 or 13, wherein the amount of oxygen required for partially oxidizing said carbonaceous feedstock is decreased.

16. The process of claim 12 or 13, wherein said hydrogen-rich gas stream is utilized as a feedstock for a chemical production process that may comprise a Fischer-Tropsch process, or a process for the production of methanol, methyl acetate, urea, urea ammonium nitrate, ammonia or hydrogen.

* * * * *